US008419609B2

(12) United States Patent
Shambaugh, Jr. et al.

(10) Patent No.: US 8,419,609 B2
(45) Date of Patent: Apr. 16, 2013

(54) IMPELLER FOR A ROTARY VENTRICULAR ASSIST DEVICE

(75) Inventors: Charles R. Shambaugh, Jr., Coral Gables, FL (US); Kartikeyan Trichi, Hollywood, FL (US); Jeffrey A. LaRose, Parkland, FL (US)

(73) Assignee: Heartware Inc., Miami Lakes, FL (US)

( * ) Notice: Subject to any disclaimer, the term of this patent is extended or adjusted under 35 U.S.C. 154(b) by 0 days.

(21) Appl. No.: 11/243,722

(22) Filed: Oct. 5, 2005

(65) Prior Publication Data

US 2007/0078293 A1    Apr. 5, 2007

(51) Int. Cl.
*A61M 1/12*    (2006.01)
(52) U.S. Cl.
USPC ............................................ 600/16; 623/3.14
(58) Field of Classification Search .................... 623/3.1, 623/3.13, 3.14, 3.15, 3.24, 3.29
See application file for complete search history.

(56) References Cited

U.S. PATENT DOCUMENTS

| | | | |
|---|---|---|---|
| 50,714 A | 10/1875 | Jacob | |
| 2,941,477 A | 6/1960 | Dalton | |
| 3,426,721 A | 2/1969 | Justinien | |
| 3,608,088 A | 9/1971 | Dorman et al. | |
| 3,685,059 A | 8/1972 | Bokros et al. | |
| 4,437,815 A | 3/1984 | McMullen | |
| 4,589,822 A * | 5/1986 | Clausen et al. | 415/174.3 |
| 4,595,390 A | 6/1986 | Hakim et al. | |
| 4,615,691 A | 10/1986 | Hakim et al. | |
| 4,625,712 A | 12/1986 | Wampler | |
| 4,642,036 A * | 2/1987 | Young | 416/179 |
| 4,688,998 A | 8/1987 | Olsen et al. | |
| 4,753,221 A | 6/1988 | Kensey et al. | |
| 4,817,586 A | 4/1989 | Wampler et al. | |
| 4,846,152 A | 7/1989 | Wampler et al. | |
| 4,906,229 A | 3/1990 | Wampler et al. | |
| 4,908,012 A | 3/1990 | Moise et al. | |
| 4,919,647 A | 4/1990 | Nash | |
| 4,927,407 A | 5/1990 | Dorman | |
| 4,944,722 A | 7/1990 | Carriker et al. | |
| 4,994,078 A | 2/1991 | Jarvik | |
| 4,995,857 A | 2/1991 | Arnold | |
| 5,061,256 A | 10/1991 | Wampler et al. | |
| 5,092,879 A | 3/1992 | Jarvik | |
| 5,112,200 A | 5/1992 | Isaacson et al. | |
| 5,209,650 A | 5/1993 | Lemieux | |
| 5,211,546 A | 5/1993 | Isaacson et al. | |
| 5,290,227 A | 3/1994 | Pasque | |

(Continued)

FOREIGN PATENT DOCUMENTS

GB    1067054    4/1967

OTHER PUBLICATIONS

MMPA Standard No. 0100-00; Standard Specifications for Permanent Magnet Materials; (Magnetic Material Producers Association; (29 pgs).

(Continued)

*Primary Examiner* — Joseph Dietrich
(74) *Attorney, Agent, or Firm* — John P. White; Cooper & Dunham LLP

(57) ABSTRACT

An impeller for a blood pump such as a magnetically driven, rotary ventricular assist device for pumping blood of a patient, the impeller being substantially entirely made of an alloy which consists essentially of about 70-80 weight percent of platinum and 20-30 weight percent of cobalt.

13 Claims, 4 Drawing Sheets

U.S. PATENT DOCUMENTS

| | | | |
|---|---|---|---|
| 5,290,236 | A | 3/1994 | Mathewson |
| 5,344,443 | A | 9/1994 | Palma et al. |
| 5,376,114 | A | 12/1994 | Jarvik |
| 5,385,581 | A | 1/1995 | Bramm et al. |
| 5,501,574 | A | 3/1996 | Raible |
| 5,527,159 | A | 6/1996 | Bozeman, Jr. et al. |
| 5,588,812 | A | 12/1996 | Taylor et al. |
| 5,613,935 | A | 3/1997 | Jarvik |
| 5,678,306 | A | 10/1997 | Bozeman, Jr. et al. |
| 5,692,882 | A | 12/1997 | Bozeman, Jr. et al. |
| 5,707,218 | A | 1/1998 | Maher et al. |
| 5,713,727 | A | 2/1998 | Veronesi et al. |
| 5,746,709 | A | 5/1998 | Rom et al. |
| 5,776,190 | A | 7/1998 | Jarvik |
| 5,824,070 | A | 10/1998 | Jarvik |
| 5,840,070 | A | 11/1998 | Wampler |
| 5,888,241 | A | 3/1999 | Jarvik |
| 5,911,685 | A | 6/1999 | Seiss et al. |
| 5,924,848 | A | 7/1999 | Izraelev |
| 5,941,813 | A | 8/1999 | Sievers et al. |
| 5,947,892 | A * | 9/1999 | Benkowski et al. ............ 600/16 |
| 5,965,089 | A | 10/1999 | Jarvik et al. |
| 6,015,272 | A | 1/2000 | Antaki et al. |
| 6,058,593 | A | 5/2000 | Siess |
| 6,068,588 | A | 5/2000 | Goldowsky |
| 6,100,618 | A * | 8/2000 | Schoeb et al. ............... 310/90.5 |
| 6,116,862 | A | 9/2000 | Rau |
| 6,120,537 | A | 9/2000 | Wampler |
| 6,135,729 | A | 10/2000 | Aber |
| 6,155,969 | A | 12/2000 | Schima et al. |
| 6,176,822 | B1 | 1/2001 | Seiss et al. |
| 6,200,260 | B1 | 3/2001 | Bolling |
| 6,227,797 | B1 | 5/2001 | Watterson et al. |
| 6,227,820 | B1 | 5/2001 | Jarvik |
| 6,234,635 | B1 | 5/2001 | Seitzinger et al. |
| 6,234,772 | B1 | 5/2001 | Wampler et al. |
| 6,234,998 | B1 | 5/2001 | Wampler |
| 6,244,835 | B1 | 6/2001 | Antaki et al. |
| 6,247,892 | B1 | 6/2001 | Kazatchkov et al. |
| 6,250,880 | B1 | 6/2001 | Woodward et al. |
| 6,254,359 | B1 | 7/2001 | Aber |
| 6,299,575 | B1 | 10/2001 | Bolling |
| 6,306,116 | B1 | 10/2001 | Hancock |
| 6,368,083 | B1 | 4/2002 | Wampler |
| 6,387,037 | B1 | 5/2002 | Bolling et al. |
| 6,390,969 | B1 | 5/2002 | Bolling et al. |
| 6,428,464 | B1 | 8/2002 | Bolling et al. |
| 6,439,845 | B1 | 8/2002 | Veres |
| 6,447,265 | B1 | 9/2002 | Antaki et al. |
| 6,447,266 | B2 | 9/2002 | Antaki et al. |
| 6,527,521 | B2 | 3/2003 | Noda |
| 6,527,699 | B1 | 3/2003 | Goldowsky |
| 6,530,876 | B1 | 3/2003 | Spence |
| 6,595,743 | B1 | 7/2003 | Kazatchkov et al. |
| 6,610,004 | B2 | 8/2003 | Viole et al. |
| 6,641,378 | B2 | 11/2003 | Davis et al. |
| 6,685,621 | B2 | 2/2004 | Bolling et al. |
| 6,688,861 | B2 | 2/2004 | Wampler |
| 6,716,157 | B2 | 4/2004 | Goldowsky |
| 6,716,189 | B1 | 4/2004 | Jarvik et al. |
| 6,717,311 | B2 | 4/2004 | Locke |
| 6,719,791 | B1 | 4/2004 | Nusser et al. |
| 6,752,602 | B2 | 6/2004 | Eistrup et al. |
| 6,794,789 | B2 | 9/2004 | Siess et al. |
| 6,869,567 | B2 | 3/2005 | Kretchmer |
| 6,889,082 | B2 | 5/2005 | Bolling et al. |
| 7,011,620 | B1 | 3/2006 | Siess |
| 7,021,905 | B2 | 4/2006 | Torrey et al. |
| 7,070,398 | B2 | 7/2006 | Olsen et al. |
| 7,229,258 | B2 | 6/2007 | Wood et al. |
| 7,699,586 | B2 | 4/2010 | LaRose et al. |
| 2004/0241019 | A1 | 12/2004 | Goldowsky |
| 2006/0036127 | A1 | 2/2006 | Delgado, III |
| 2006/0245959 | A1 | 11/2006 | LaRose et al. |
| 2007/0100196 | A1 | 5/2007 | Shambaugh, Jr. et al. |
| 2010/0069847 | A1 | 3/2010 | LaRose et al. |

OTHER PUBLICATIONS

International Search Report issued by the International Searching Authority (ISA/US) in connection with International Application No. PCT/US2005/42495.

Written Opinion of the International Searching Authority issue by the International Searching Authority (ISA/US) in connection with International Application No. PCT/US2005/42495.

International Preliminary Report on Patentability issued by the International Bureau of WIPO on Apr. 8, 2008 in connection with International Application No. PCT/US2005/42495.

International Search Report issued by the International Searching Authority (ISA/US) in connection with International Application No. PCT/US2005/35964.

Written Opinion of the International Searching Authority issue by the International Searching Authority (ISA/US) in connection with International Application No. PCT/US2005/35964.

International Search Report issued by the International Searching Authority (ISA/US) in connection with International Application No. PCT/US2006/21544.

Written Opinion of the International Searching Authority issue by the International Searching Authority (ISA/US) in connection with International Application No. PCT/US2006/21544.

International Preliminary Report on Patentability issued by the International Bureau of WIPO on Apr. 8, 2008 in connection with International Application No. PCT/US2006/21544.

Office Action issued Mar. 17, 2008 in connection with U.S. Appl. No. 11/003,810, filed Dec. 3, 2004.

Final Office Action issued Dec. 10, 2008 in connection wit U.S. Appl. No. 11/003,810, filed Dec. 3, 2004.

Advisory Action issued Apr. 27, 2009 in connection with U.S. Appl. No. 11/003,810, filed Dec. 3, 2004.

Notice of Allowance issued Aug. 28, 2009 in connection with U.S. Appl. No. 11/003,810, filed Dec. 3, 2004.

Notice of Allowance issued Jan. 12, 2010 in connection with U.S. Appl. No. 11/003,810, filed Dec. 3, 2004.

Office Action issued Mar. 20, 2008 in connection with U.S. Appl. No. 11/118,551, filed Apr. 29, 2005.

Final Office Action issued Oct. 23, 2008 in connection with U.S. Appl. No. 11/118,551, filed Apr. 29, 2005.

Office Action issued Apr. 17, 2009 in connection with U.S. Appl. No. 11/118,551, filed Apr. 29, 2005.

Office Action issued Sep. 22, 2009 in connection with U.S. Appl. No. 11/445,963, filed Jun. 2, 2006.

Final Office Action issued Nov. 18, 2009 in connection with U.S. Appl. No. 11/118,551, filed Apr. 29, 2005.

Advisory Action issued Feb. 12, 2010 in connection with U.S. Appl. No. 11/118,551, filed Apr. 29, 2005.

Office Action issued Jul. 12, 2010 in connection with U.S. Appl. No. 11/118,551, filed Apr. 29, 2005.

Notice of Allowance issued Dec. 9, 2010 in connection with U.S. Appl. No. 11/118,551, filed Apr. 29, 2005.

Office Action issued Jan. 19, 2010 in connection with U.S. Appl. No. 11/445,963, filed Jun. 2, 2006.

Final Office Action issued Aug. 16, 2010 in connection with U.S. Appl. No. 11/445,963, filed Jun. 2, 2006.

Notice of Allowance issued Feb. 17, 2011 in connection with U.S. Appl. No. 11/445,963, filed Jun. 2, 2006.

* cited by examiner

IMPELLER FOR A ROTARY VENTRICULAR ASSIST DEVICE

BACKGROUND OF THE INVENTION

Various designs of blood pumps are known for pumping the blood of a patient to assist a failing heart in the pumping. Particularly, implantable, magnetically driven, rotary ventricular assist devices (VADs) are blood pumps which may, if desired, be implanted in the patient to provide assistance in the pumping for hearts that are afflicted with congestive heart failure or the like. Examples of such pumps are rotary type blood pumps as disclosed in U.S. Pat. Nos. 6,688,861, 6,120, 537, 6,234,998, 6,234,772 and 6,234,635.

By this invention, a blood pump impeller is provided, which impeller is magnetizable to a high degree, and which may be manufactured as a single piece, thereby eliminating assembly procedures and hermeticity concerns, which concerns are associated with a traditional approach of placing magnetic materials within an impeller casing, and laser welding closure caps to the casing, as in certain prior art techniques.

DESCRIPTION OF THE INVENTION

By this invention, an impeller for a blood pump is provided, the impeller being substantially entirely made of a magnetic alloy which typically consists essentially of about 70-80 weight percent of platinum and about 20-30 weight percent of cobalt. In some embodiments, from essentially 76-79 weight percent of platinum is present in the alloy. An "impeller" is defined as the movable, fluid driving portion of a pump.

It is also desirable for the impeller to comprise a single, integral piece, which is more easily accomplished when using an impeller of the above described alloy because, unlike certain other "high strength", permanent, magnetic alloys, this particular alloy can be easily fabricated into complex shapes, using conventional metal working and casting methods. Also, the alloy used in this invention is magnetically isotropic, so that parts can be easily magnetized with a plurality of magnetic poles in any geometric orientation. These characteristics allow the impeller to be fabricated from a solid piece of the alloy used in this invention, thus eliminating the need to build assemblies of magnets and support structures, as in the case of prior art ventricular assistance devices, with a resulting reduction of manufacturing costs. Additionally, the alloy used in this invention is biocompatible, and has high resistance to corrosion, also having a Rockwell hardness on the order of 31 Rc, which eliminates the need for a hard, outer coating.

The impeller, typically as a single piece of raw material prior to fabrication, is preferably heat treated so that the alloy of the impeller can achieve enhanced magnetic and mechanical properties. Such a heat treatment process may be a known process as described in British Patent No. 1,067,054. The impeller is then magnetized by a known technique, and exhibits excellent magnetic properties. Such heat treated alloys are commercially available.

In some embodiments, the alloy may contain essentially from 21-24 weight percent of cobalt in the alloy.

The impeller of this invention may be used in a magnetically driven, rotary ventricular assist device (VAD) for pumping blood of a patient, with the device carrying the impeller of this invention. However, by this invention, other, nonrotary impellers may be provided for blood pumps, for example a positive displacement, ventricular assist device, where a magnetic piston is used made of the alloy in accordance with this invention.

Preferably, the ventricular assist device (VAD) of this invention may be implantable in the patient, and may be of any known design, for example as disclosed in the above U.S. Patents. The rotary, ventricular assist device for pumping blood of the patient may supplement the blood pumping action of the patient's heart, or it may serve as a full substitute for the blood pumping action of the patient's heart, comprising a full artificial heart. The VAD device may provide an axial, pumped blood flow as shown below, or it may provide a centrifugal, pumped blood flow as in U.S. Pat. No. 6,688, 861, the disclosures of which are incorporated by reference.

While it is known to use magnets made of platinum-cobalt alloys in blood pumps, as in Dorman et al. U.S. Pat. No. 3,608,088, by this invention, essentially the entire impeller of the pump is made of the alloy specified, rather than stainless steel or the like. Thus, implantable blood pumps such as VAD pumps with the impeller of this invention exhibit significant advantages, as described above.

DESCRIPTION OF SPECIFIC EMBODIMENTS

Referring to FIGS. 1-5, a single piece impeller or rotor 14, positioned in an axial flow, ventricular assist device (VAD) 10, is disclosed. The integral, one-piece impeller 14 disclosed comprises a homogeneous alloy of essentially 77.6 weight percent platinum, the balance being substantially cobalt.

Figure 4:
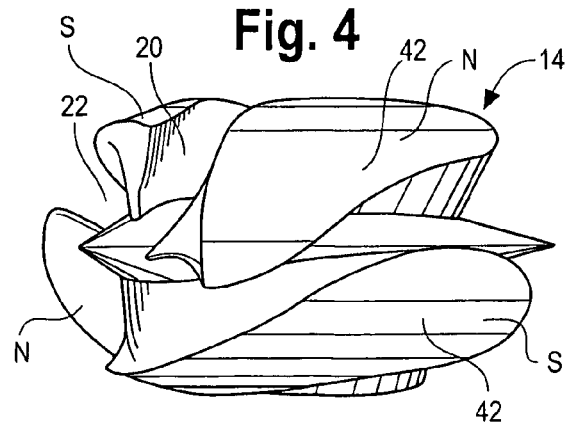

Impeller 14 is conventionally heat treated to achieve good magnetic properties, and magnetized, with the North (N) and South (S) magnetic poles being as indicated on bladelike projections 20 (FIG. 4).

The heat treated, homogeneous alloy used was purchased from Engelhard Corporation of Iselin, N.J. The single-piece impeller 14 may be formed by machining from a single piece of the purchased alloy, which was then magnetized in a conventional manner in the pole pattern indicated, for example as performed by Magnet Applications of Horsham, Pa. The impeller is used in VAD 10 as described below.

Rotor 14 is positioned within the lumen of pump housing 12, and acts as an impeller, having a hydrodynamic surface (specifically a series of hydrodynamic surfaces 16 that tend to propel blood in an axial direction as indicated by arrow 18) as rotor 14 is rotated clockwise. This blood pump 10 may be connected to the patient's vascular system to serve as a rotary ventricular assist device (VAD).

Rotor/impeller 14 comprises radially outwardly extending, blade-like projections 20 having side walls 16 that define generally longitudinally extending spaces 22 between the projections 20. The projections 20 and their side walls 16 are shaped to form curves in the longitudinally extending spaces 22 which are of a shape tending to drive blood in axial direction 18 as rotor/impeller 14 is rotated (clockwise in the embodiment of FIG. 1).

Figure 5:
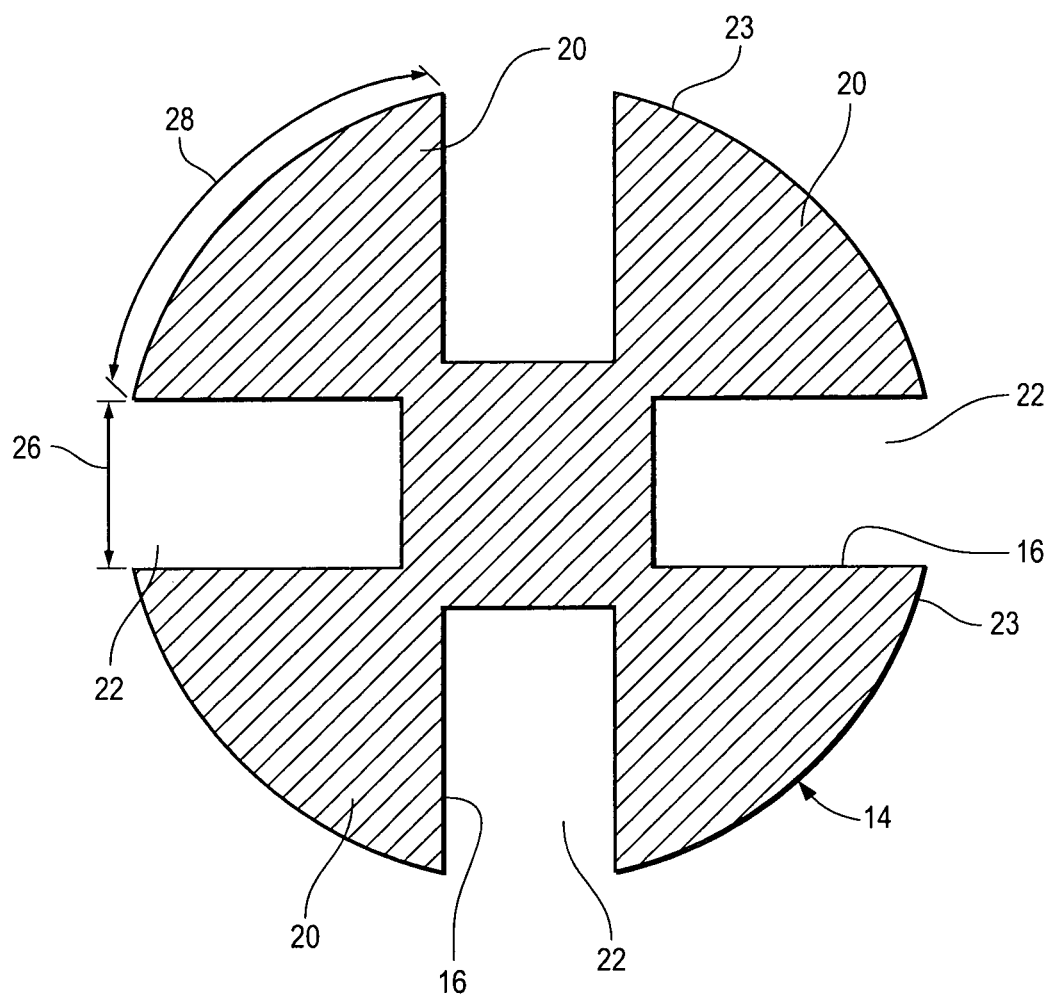
FIG. 5 is a sectional view taken along line 5-5 of FIG. 2.

It will be noted, particularly from FIG. 5, that the longitudinally extending spaces 22 collectively have, adjacent to radially outer periphery 23 at the outer circumference of rotor 14, a collective, total circumferential width that is substantially less than the collective, total circumferential width of the projections 20 at the same radially outer periphery 23. This is illustrated by peripheral width 26, illustrated on one of the longitudinally extending spaces 22 in FIG. 5, when compared with peripheral width 28 of adjacent, blade-like projections 20. Collectively, the four widths 26 of each of the spaces 22 comprise a collective, total width of all four longitudinally extending spaces 22. Four times the distance of arc 28 represents the collective, total width of the four blade-like projections 20. It can be readily seen that the collective total width of the longitudinally extending spaces 22 is substantially less at periphery 23 than the collective, total width of the respective blade-like projections 20, in the embodiment of FIGS. 1-5.

Figure 1:
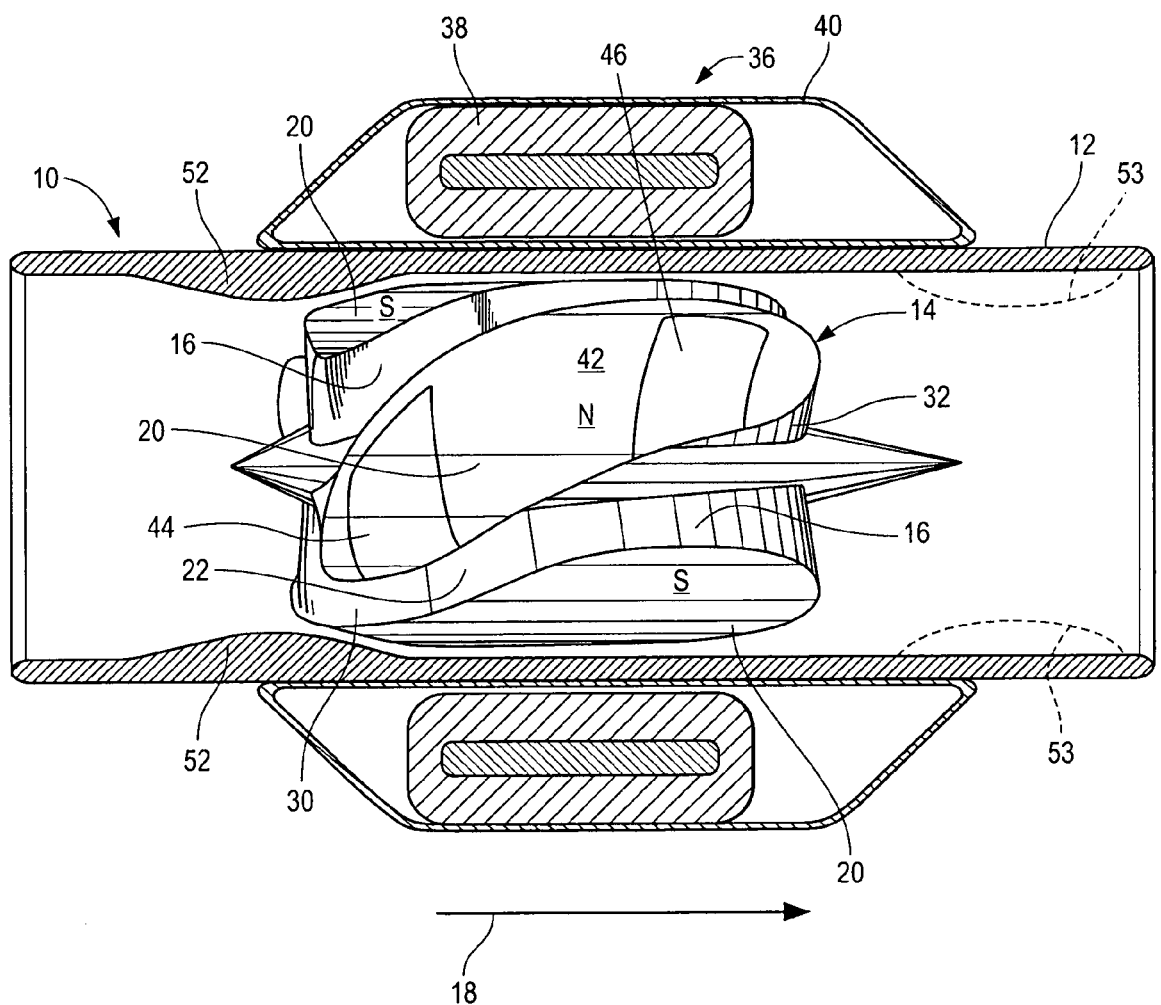
FIG. 1 is an enlarged, longitudinal sectional view of an implantable, sealed rotary blood pump of this invention.
Figure 2:
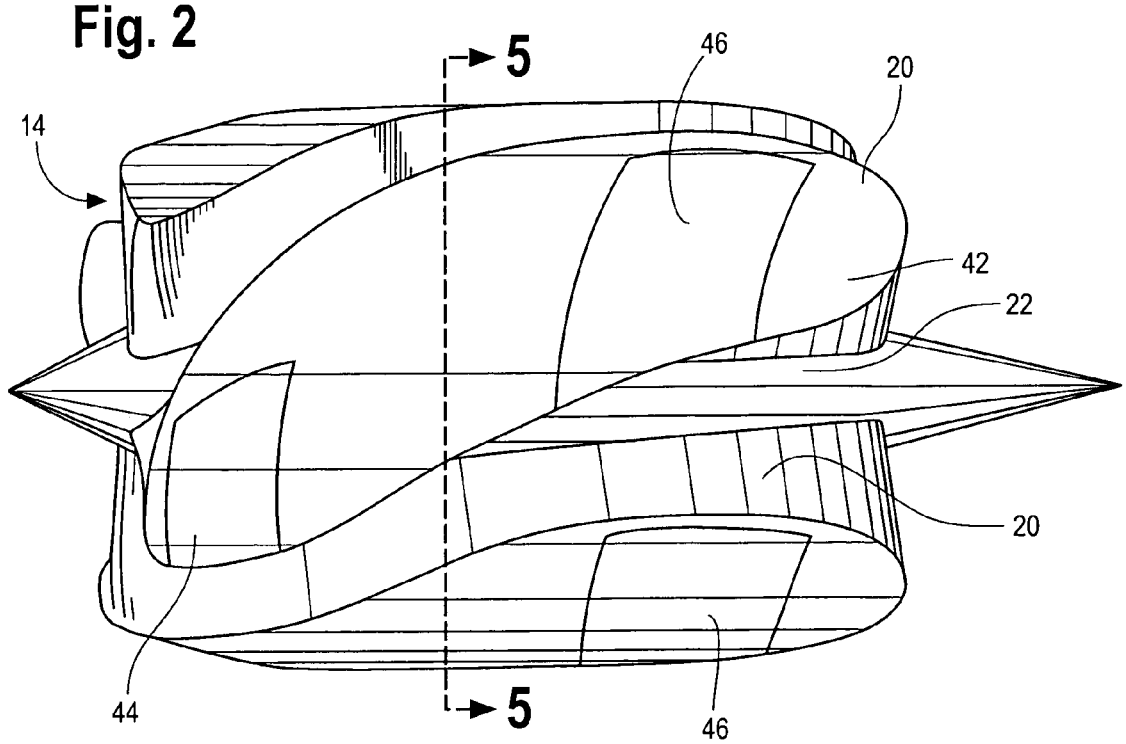
FIG. 2 is a further, enlarged perspective view of the rotary impeller of the pump of FIG. 1.
Figure 3:
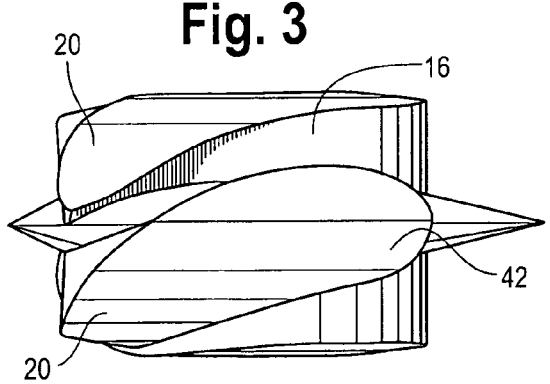
FIGS. 3 and 4 are additional side views of the impeller of FIG. 2 in differing positions.

It is preferred for transverse sections (FIG. 5) of longitudinally extending spaces 22 to have generally parallel side walls 16, although it can also be seen from FIG. 1 and other drawings that the overall width of longitudinally extending spaces 22 may vary along their lengths, being particularly somewhat narrower at upstream areas 30, and wider at downstream areas 32, as shown in FIG. 1. Thus, it can be seen from particularly FIG. 1 that clockwise rotation of rotor 14 will result in a flow of blood within the lumen of housing 12 from left to right in direction 18.

Blood pump 10 further comprises a motor, which includes magnetized, thick, wing-like projections 20, having the respective poles, N. S. The motor also comprises a motor stator 36 (FIG. 1), including an electrically conductive coil 38, within an enclosure 40, which surrounds housing 12 and rotor 14, and serves to rotate rotor 14 by the conventional application of electric power to coil 38, which is converted via magnetic force to torque, causing rotor 14 to rotate clockwise. The specific technology for accomplishing this may be similar to that which is well known in the prior art.

FIGS. 1-4 show radially outer faces 42 of blade-like projections 20, also showing a pair of hydrodynamic bearings 44, 46, which may be defined on projections 20 in the embodiment of FIGS. 1-5, and which use fluid pressure to cause rotor 14 to be centered in the lumen of tubular housing 12 as rotor 14 rotates, in a manner generally shown in FIG. 1, without the need for physical bearings utilizing rubbing, solid surfaces.

Thus, rotor 14 rotates, being held away from the inner wall of housing 12 by hydrodynamic bearings 44, 46 on each of the wing-like projections 20. At the rear of rotor 14, an inner, annular ring 52 of housing 12 (FIG. 1) is seen to project a bit inwardly from the inner wall cylinder housing 12, to limit the leftward motion of rotor 14. Ring 52 may, if desired, comprise an annular series of spaced projections, or it may comprise a solid ring, with hydrodynamic bearings 44 serving to prevent contact between rotor 14 and ring 52 as the pump is operating with clockwise rotation of rotor 14. A similar, annular ring 53 may be defined near the other end of housing 12 for similar purpose.

Of course, it is within the scope of this invention to design a rotor which can rotate in the counterclockwise direction, making use of the principles and advantages as described above.

If desired, the stator 36 may comprise a separate, hermetically sealed, coil motor that slides over tubular housing 12 in position, and is secured thereto. Otherwise, stator and coil 38 may be integrally attached to housing 12.

Each of thrust bearings 44, 46 define a recessed, curved outer surface which forms a recessed end portion relative to the outer face 42 of each projection 20, located at the forward end of each bearing 44, 46 from the viewpoint of the (clockwise) spin of the rotor 14a, so that recessed end forms a leading edge of rotation. The recessed surface then tapers in a gradual, curved manner outwardly to the rear end of each thrust bearing 44, 46, at which point, the bearing surface is not recessed, or only very slightly recessed, in a manner similar to that described in Wampler et al. U.S. Pat. No. 6,234,772.

Thus, as the rotor rotates, the respective thrust bearings, 44, 46 on each projection 20 scoop blood into a cross-sectional, recessed area of each bearing that decreases going from end to end, the effect of this being to pressurize the blood, and to thus repel each projection 20 from the inner wall of housing 12 as the rotor rotates. Since the rotor is spaced from the walls of housing 12, the pressurized blood is released out of each bearing by passing across the end and out the sides of the recess.

A pressure relief zone is provided at the trailing rotary end of each rotating projection 20.

Basically, the VAD of FIGS. 1-5 is similar, but for the improvements disclosed herein, to that disclosed in LaRose et al. U.S. patent application Ser. No. 11/003,810, filed Dec. 3, 2004, the disclosures of which are incorporated by reference.

Figure 6:
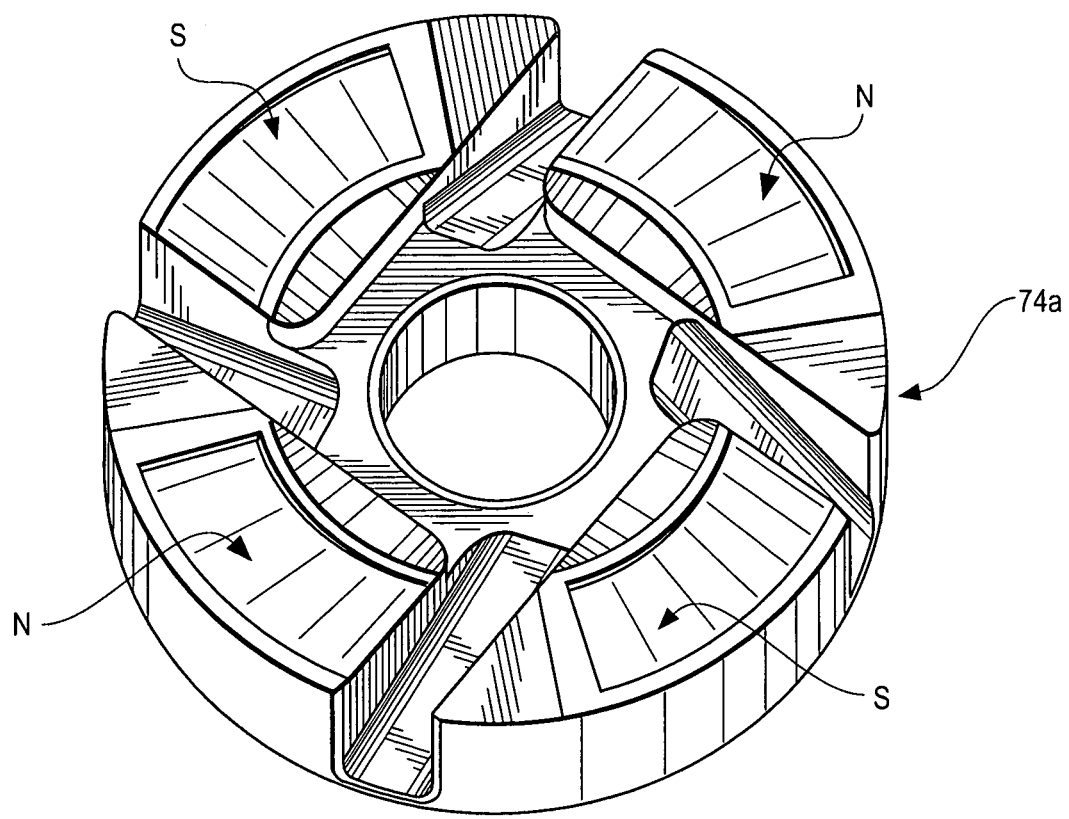
FIG. 6 is a perspective view of a single piece impeller for a centrifugal flow ventricular assist device.

Referring to FIG. 6, a one-piece impeller 74a for a centrifugal flow ventricular assist device is shown, a particular VAD device in which the impeller operates being as described in U.S. Pat. No. 6,688,861, particularly FIG. 12. This one-piece, centrifugal flow impeller 74a may also be made of the above described, homogeneous alloy of 77.6 weight percent platinum, with the balance being essentially cobalt, being conventionally heat treated and quenched by the manufacturer to achieve its good magnetic properties. The respective magnetic poles N, S are as shown in FIG. 6, and may be formed by a conventional magnetization process. The impeller is then used in a VAD of an appropriate type.

This invention is also applicable to mixed flow ventricular assist device impellers as well.

Thus, by this invention, one piece impellers for blood pumps, and particularly VADs which may be implanted into the patient, are provided. Because of the use of the impellers of this invention, the impellers may have very strong magnetic properties, for strong electromagnetic coupling, thus permitting a compact VAD design with high efficiency. They may also, unlike certain other permanent magnet alloys which are hard and brittle, be easily fabricated into complex shapes using conventional metal working and casting methods. They are also magnetically isotropic, so that parts can be easily magnetized with a plurality of magnetic poles positioned in any geometric orientation. These characteristics allow components to be fabricated from a single, solid piece of platinum-cobalt alloy, thus eliminating the need to build assemblies of magnets and support structures, for a reduction of manufacturing costs. The alloy used in this invention is biocompatible, has a high resistance to corrosion, and is very hard, on the order of a Rockwell hardness of 31 Rc, thus eliminating the need for an outer, hardened coating.

The above has been offered for illustrative purposes only, and is not intended to limit the scope of the invention of this application, which is as defined in the claims below.

That which is claimed is:

1. A magnetically driven rotary ventricular assist device implantable in a patient and configured to pump blood of the patient, said device comprising:

a rotatable body formed entirely of heat treated biocompatible magnetizable platinum and cobalt alloy, said rotatable body having a shape by which each of a plurality of blood flow channels formed therein is configured to direct blood traversing a channel away from said body when said body is rotating within the assist device, selected portions of said body of magnetizable alloy being subjected to magnetization establishing magnetic bearings for support of said body when said body is rotating within the ventricular assist device and for inducing north magnetic poles and south magnetic poles for effecting one or more of a magnetic drive mechanism and an axial or radial orientation of said body within the assist device while rotating.

2. The device of claim 1 which provides a centrifugal, pumped blood flow.

3. The device of claim 1 which provides an axial, pumped blood flow.

4. The device of claim 1, wherein said biocompatible magnetizable alloy consists essentially of about 70-80 weight percent of platinum and about 20-30 weight percent of cobalt.

5. The device of claim 4 in which said body is formed from 76-79 wt. percent of platinum.

6. The device of claim 1 in which land areas are formed on said rotatable body between said blood flow channels.

7. The device of claim 6 in which each of said land areas comprises at least one north or at least one south pole.

8. The device of claim 6 in which said land areas are each provided with alternating north and south poles.

9. A magnetically driven, rotary ventricular assist device, said device implantable in a patient and configured to pump blood of the patient, said device comprising:

a body formed entirely of biocompatible magnetizable alloy consisting essentially of about 70-80 weight percent of platinum and about 20-30 weight percent of cobalt, to enable strong electromagnetic coupling, said body of biocompatible magnetizable alloy being shaped to define a blood pumping impeller having a plurality of blood flow channels defining land areas therebetween, selected portions f said body of magnetizable alloy being subjected to magnetization whereby said blood pumping impeller comprises a plurality of north poles and a plurality of south poles, said magnetization arranging at least one of said north poles or at least one of said south poles on each of said land areas.

10. The device of claim 9, in which the alloy of the impeller is in a heat-treated state for improved magnetic properties.

11. The device of claim 9, in which from essentially 76-79 weight percent of platinum is present in the alloy.

12. The device of claim 9, which provides a centrifugal, pumped blood flow.

13. The device of claim 9 which provides an axial, pumped blood flow.

* * * * *